United States Patent [19]

Blanco et al.

[11] Patent Number: 5,005,559

[45] Date of Patent: Apr. 9, 1991

[54] VIDEO-GRAPHIC ARTHROSCOPY SYSTEM

[75] Inventors: Ernesto E. Blanco, Belmont; Pascal R. Chesnais, Allston, both of Mass.; Phyllis K. Kristal, Glen Cove, N.Y.; Andrew B. Lippman, Salem, Mass.

[73] Assignee: Massachusetts Institute of Technology, Cambridge, Mass.

[21] Appl. No.: 386,343

[22] Filed: Jul. 27, 1989

[51] Int. Cl.$^5$ .............................................. A61B 1/06
[52] U.S. Cl. .......................................... 128/4; 356/241
[58] Field of Search ......................................... 128/3–8; 356/241

[56] References Cited

U.S. PATENT DOCUMENTS

| | | | |
|---|---|---|---|
| 4,078,864 | 3/1978 | Howell | 356/241 X |
| 4,277,168 | 2/1981 | Oku | 356/241 X |
| 4,340,302 | 6/1982 | Oku | 128/4 X |
| 4,407,277 | 10/1983 | Ellison | 128/82 |
| 4,413,278 | 11/1983 | Feinbloom | 358/93 |
| 4,572,594 | 2/1986 | Schwartz | 312/209 |
| 4,586,079 | 4/1986 | Cooper. Jr. et al. | 356/241 X |
| 4,590,923 | 1/1986 | Watanabe | 128/6 |
| 4,689,449 | 8/1987 | Rosen | 200/6 |

Primary Examiner—Benjamin Layno
Attorney, Agent, or Firm—Thomas J. Engellenner

[57] ABSTRACT

A position sensing system which allows the arthroscopist to readily determine the location of an arthroscope's tip in relation to the point of entry has been developed. The position sensing apparatus can be employed in conjunction with a graphics module to display the location of the arthroscope in real time and provide perspective views of the instrument's location.

5 Claims, 2 Drawing Sheets

VIDEO-GRAPHIC ARTHROSCOPY SYSTEM

BACKGROUND OF THE INVENTION

The technical field of this invention is arthroscopy and, in particular, methods and apparatus for displaying the location of an arthroscope during use.

Arthroscopy allows for direct examination of biological structures (most commonly, the knee joint, but also the hip, shoulder, elbow and hand, as well) utilizing tiny incisions through which the arthroscope is inserted. The arthroscope contains illuminating glass fibers and a series of magnifying optical lenses that project light into the joint and relay a magnified image back to the clinician.

Conventional arthroscopes present a number of problems to the inexperienced user. Since the view from the probe is circular, it is difficult to determine the scope's orientation from the scene without actually moving the scope. Moreover, the arthroscope typically has an offset of 30°; hence, the center of view is not in the direction of arthroscope motion into or out of the biological structure.

Additionally, when the arthroscope is rotated, the motion needed to manipulate the probe is not always obvious. For example, if the probe is rotated 180° such that the view is "upside down" relative to the user, the motion needed to manipulate the probe is completely reversed; to move up, the user must lift the arthroscope's distal end up.

Even in the hands of a skilled practioner, the fish-eye, two-dimensional view of the arthroscope can often be uninformative; objects of interest within the joint are often not found in the field of view or hidden by other biological structures.

There exists a need for better arthroscopy systems for non-invasive and accurate examination of bone joints and other biological structures. An object of the present invention is to provide better display systems for orthopedic surgeons in the practice of arthroscopy. Another object of the present invention is to provide a teaching tool for the training of arthroscopists.

Yet another object of the invention is to provide visual systems which can enhance spatial visualization of arthroscopy, including the coordination of images seen by the surgeon through the arthroscope and varying reference points, such as natural bone structures and/or other instruments that are inserted into the observation region to perform surgical procedures.

SUMMARY OF THE INVENTION

A position sensing system which allows the arthroscopist to readily determine the location of an arthroscope's tip in relation to the point of entry has been developed. The position sensing apparatus can be employed in conjunction with a graphics module to display the location of the arthroscope in real time and provide perspective views of the instrument's location.

In one aspect of the invention, a sensing apparatus is disclosed for monitoring the four degrees of freedom (X, Y, Z and rotation) possessed by the arthroscope. A double-yoke gimbel structure is adapted for positioning on a joint, such as the knee, in order to measure the pivoting of the arthroscope (in the X and Y directions) about the point of entry. Rotation of the arthroscope is measured by a sensor mounted on a sleeve which is fixed relative to the rotation of the arthroscope. Finally, penetration of the arthroscope is measured by a fourth sensor which detects relative motion of the arthroscope into or out of the patient's joint relative to a fixed reference point. This sensing apparatus provides an electrical output which can precisely define the location of the arthroscope's tip at all times.

In another aspect of the invention, the electrical output of the position sensor is employed in conjunction with a graphics processor to generate perspective "bird's eye" views of the arthroscope in relation to an actual or a generic structure showing the major components of the joint. These graphic views can be employed for surgical or teaching purposes. In a further aspect of the invention, processor-generated graphic images can be merged with the actual video display of the arthroscope to provide a composite picture.

The invention will next be described in connection with certain illustrated embodiments. However, it should be clear to those skilled in the art that various changes, additions and subtractions can be made without departing from the spirit or the scope of the invention.

DESCRIPTION

Figure 1:
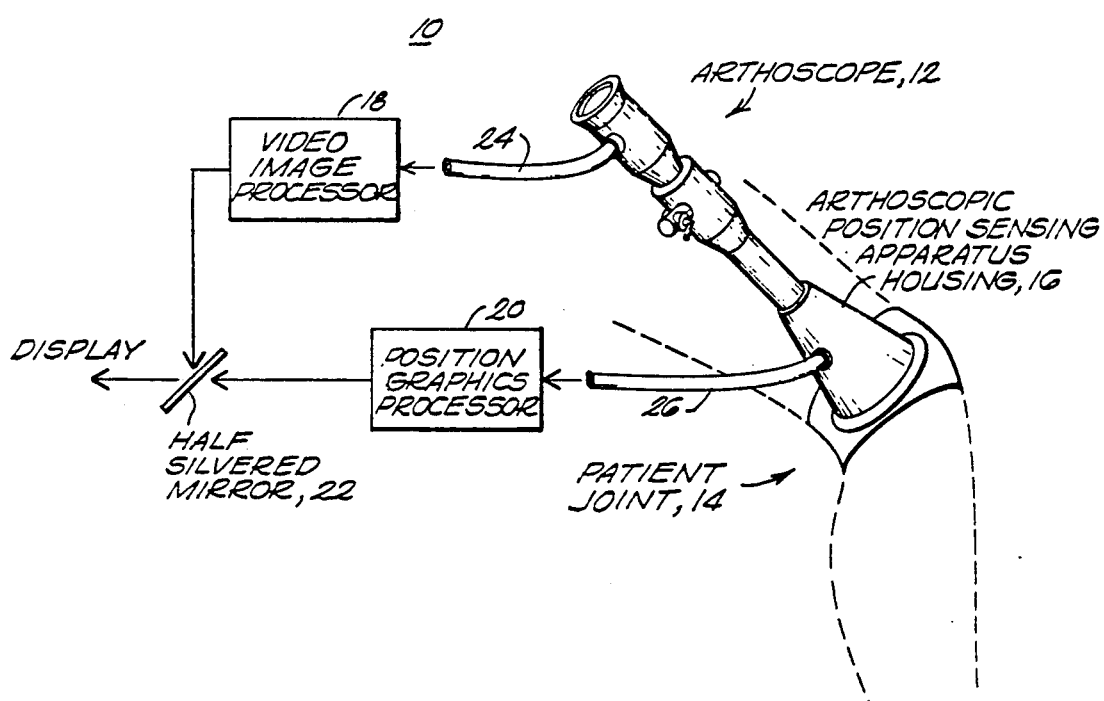
FIG. 1 is an overall schematic block diagram of a video-graphic arthroscopy system according to the invention.

In FIG. 1, a video-graphic arthroscopy system 10 is shown including an arthroscope 12 and a housing 16 for the position sensing apparatus which is attached to a patient's joint 14 (shown in phantom). The arthroscope includes conventional saline injection means (not shown) to distend the joint and also a conventional source of illumination (not shown) to illuminate the joint. Light from the observation region is transmitted via optical fiber 24 to a video-image processor 18, which generates a video image of the biological structures under observation in the patient's joint.

At the same time, a position sensing apparatus in housing 16 generates electrical signals via cable 26, which are transmitted to a position graphics processor 20 to generate a display of the arthroscope's position relative to a fixed reference point (typically the point of entry). In the illustration of FIG. 1, a graphic image is generated by the graphics processor 20 which is superimposed upon the video image using half silvered mirror 22 to provide a display for the arthroscopist.

Figure 2:
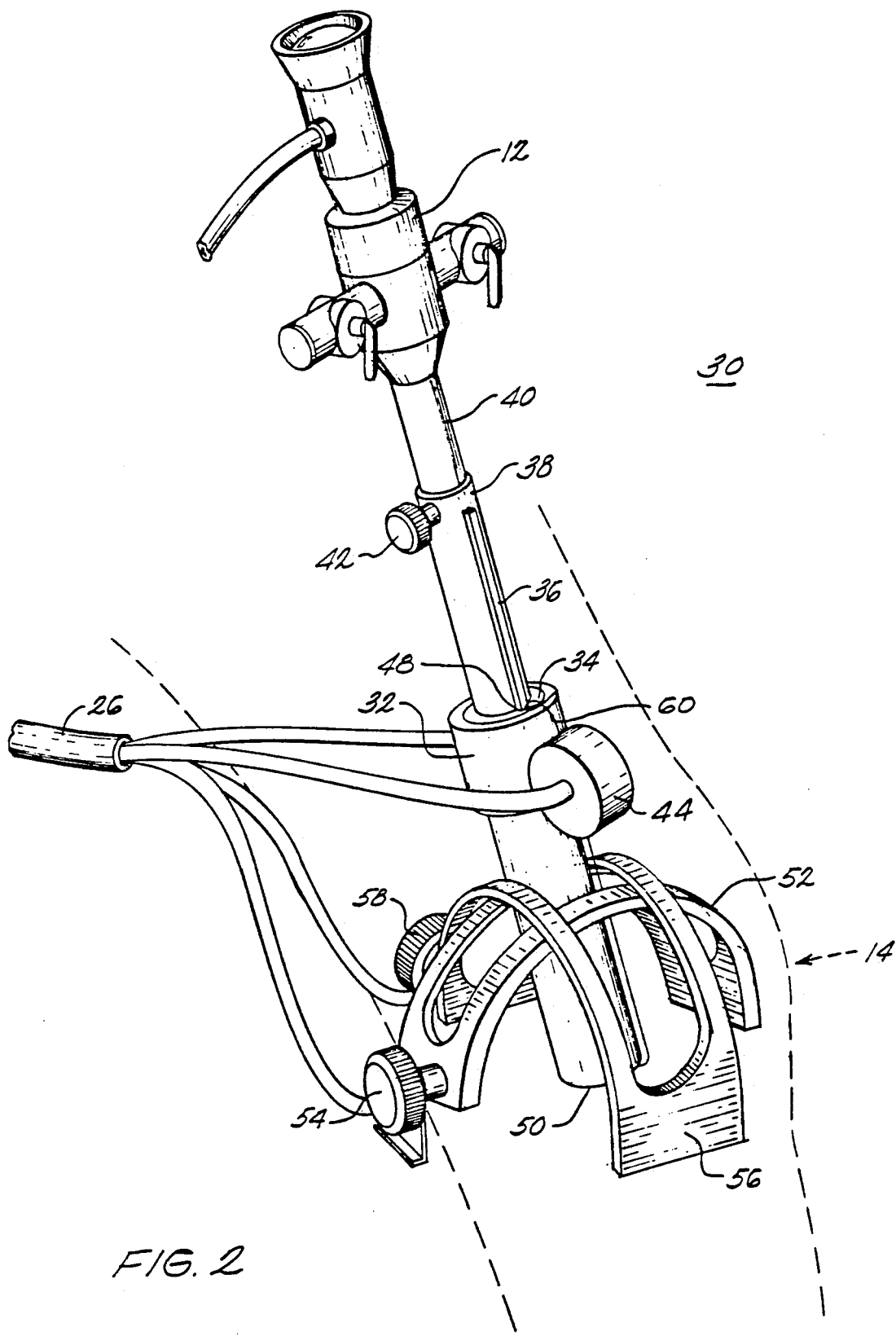
FIG. 2 is a detailed illustration of an arthroscopic position sensing apparatus according to the invention.

In FIG. 2, the position sensing apparatus 30 of the present invention is shown in more detail (with the housing removed for illustration), including a rotation sensor 32 which is mounted upon the cannula 46 of arthroscope 12. Within the rotation sensor 32, a rotor 34 includes a keyway notch 48 which mates with a keyway or spline 36 carried upon sleeve 38. The sleeve 38 is attached to sheath 40 of the arthroscope 12 by set screw 42.

A depth sensor 44 is also employed to measure the depth of penetration of the arthroscope 12 into the patient's joint. The depth sensor 44 can be attached to the cannula 46 (Or alternatively to the sleeve 38). In the illustrated embodiment, position sensing apparatus 30 utilizes depth sensor 44 and nylon line 60, coupled to sleeve 38 and wound around a spool in depth sensor 44, to provide information representative of the depth of penetration of arthroscope 12 into the patient's joint. Depth sensor 44 translates the degree to which nylon line 60 is wound or unwound from depth sensor 44 into an analog voltage which is supplied to a processor. As sleeve 38 is inserted or retracted, nylon line 60 is unwound or wound, respectively. As a result, a magnet, which is coupled to the spool in depth sensor 44, rotates correspondingly. A Hall effect sensor measures the motion of the magnet and generates a signal which is conditioned by conventional electronics. (Alternatively, the depth sensor can employ a rack and pinion-type drive mechanism, whereby a pinion gear drives the sensor and mates with a rack mounted upon sleeve 38.)

Semicircular sloted yokes 52, 56 define an X-axis and a Y-axis for measuring the tilt of the arthroscope during usage. An X-axis sensor 58 is joined to the center of rotation of the X-axis yoke 56, and a similar Y-axis sensor 54 is joined to the center of rotation of Y-axis yoke 52. The cannula 46 is disposed between the yokes 52, 56 so that the sensors 54, 58, can provide a direct relationship between sensor rotation and the angular movement (tilting) or the arthroscope 12. The two-member system effectively decouples the motion in the X and Y directions. An angular range of motion in each direction of approximately ~40 degrees is typically sufficient for arthroscopic operations.

Various commercially available sensors can be employed to measure the four degrees of motion. For example, the rotary sensor 32 has been implemented employing a rotary variable differential transformer, such as the model RA1 sensor manufactured by Transducers and Systems, Inc. (Northbranford, Conn.). The other sensors (for measuring tilt and penetration) can also employ rotary sensors or simpler devices For example, commercially available Hall effect sensors such as those manufactured by Texas Instruments (Dallas, Tex.) can be employed.

The analog voltages generated by the sensors are transmitted, via cable 26, to a processor which includes an analog to digital converter to translate the analog votage to a digital representation thereof. As detailed above, the sensor information is utilized to generate positional information of the probe of arthroscope 12 with respect to the patient's joint, and to generate computer graphics simulating objects not generally present in the patient's joint.

The processor, which can be a general purpose computer or other processing device, in conjunction with the information from the sensors can provide a computer-generated model of the joint in question. This computer graphic model can augment the video display of the arthroscope. A variety of commercially available computer graphics engines can be used, such as the Rennaissance graphics engine manufactured bY Hewlett-Packard (Andover, Mass.) for use on the HP-9000 computer, a general purpose work station built around a Motorola 68020 processor. The Rennaissance engine is capable of generating high resolution images for both 2 and 3-dimensional displays.

The graphics operations of this system can be implemented using a variety of commercially available graphics programs, such as the Hewlett-Packard Starbase graphics package. The main loop of such programs continually poles the position of the arthroscope and then performs various tasks.

In one demonstration of the system, a wire frame cross-section data base of the major bones of the knee was entered into the processor memory. The program was then configured to generate a line representing the probe and display it over the cross section. The probe orientation with respect to the wire frame illustration of the knee could then be displayed from the sensor signals by using a set of transformational matrices. In one embodiment, three orthogonal views can be presented to the viewer. (For further details on computer graphics, see Newman and Sproul, *Principles of Interactive Computer Graphics* (McGraw-Hill, 1979) and Rogers, *Procedural Elements for Computer Graphics* (McGraw-Hill, 1985) (both of which are incorporated herein by reference).

More realistic knee illustrations can, of course, be generated with appropriate graphics programs using more detailed data bases of the biological structures. In a further embodiment of the invention, such graphic displays can be merged with the video images from the arthroscope. If the video signals generated by graphics engine are incompatable with the video signals generated by the viewing probe's camera, either a standards conversion box which reduces the high resolution graphics picture to a NTSC resolution interlaced video image can be employed. Alternatively, it is possible to convert the NTSC resolution arthroscope image up to the same resolution as the graphics image, and electronically merge them.

In yet another alternatively, the two images can be optically merged using a half-silvered mirror. Use of such a mirror enables one to merge the two images, both inexpensively, and with no loss of resolution. The images are merged together by placing a mirror, which is partially reflective and transmisive, at a 45° angle in between two monitors which are perpendicular to each other. The viewer sits in front of one monitor and sees the image from the other monitor superimposed upon the first monitor's image. Various alternatives and auxiliary devices can also be incorporated into the present invention. For example, the graphics processor can include additional user input interfaces, such as a graphics tablet, mouse, knob box, button box or keyboard. These input devices can provide the user with a means of "pointing" to objects within the scene.

It will be understood that changes may be made in the above construction and the forgoing sequences of operations without departing from the spirit or scope of the invention. It is accordingly intended that all matter contained in the above description or shown in the accompanying drawings be interpreted as illustrative rather than in a limiting sense.

Having described the invention, what is claimed as new and secured by letters patent is:

1. An arthroscopic display system for displaying the location of an arthroscope during use, the display system comprising:

position-sensing means adapted for cooperation with an arthroscope for monitoring movement of the arthroscope and for generating electrical signals indicative of the movement including means for monitoring at least the tilt of the arthroscope during operation; and graphic display means electrically connected to the position-sensing means for converting the electrical signals into a graphic display of the position of the arthroscope during use.

2. The display system of claim 1 wherein the position-sensing means further includes means for monitoring penetration of the arthroscope relative to a point of entry.

3. The display system of claim 1 wherein the position-sensing means further includes means for monitoring the rotation about a longitudinal axis of the arthroscope.

4. An arthroscopic display system for displaying the location of an arthroscope during use, the display system comprising:

position-sensing means adapted for cooperation with an arthroscope for monitoring movement of the arthroscope and for generating electrical signals indicative of the movement including means for monitoring the tilt of the arthroscope relative to a point of entry; and graphic display means electrically connected to the position-sensing means for converting the electrical signals into a graphic display of the position of the arthroscope during use wherein the graphics display means further includes means for generating a perspective view of the arthroscope within its operating environment.

5. The display system of claim 4 wherein the graphic display further includes means for illustrating the arthroscope position in conjunction with an anatomic structure.

* * * * *